(12) United States Patent
Lin (10) Patent No.: US 7,458,278 B1
(45) Date of Patent: Dec. 2, 2008

(54) TORSION DETECTING MECHANISM FOR A PNEUMATIC TOOL

(75) Inventor: Tsun-Tien Lin, Wurih Township, Taichung County (TW)

(73) Assignee: Pneutech Manufacture Co., Ltd., Taichung (TW)

( * ) Notice: Subject to any disclaimer, the term of this patent is extended or adjusted under 35 U.S.C. 154(b) by 0 days.

(21) Appl. No.: 11/868,511

(22) Filed: Oct. 7, 2007

(51) Int. Cl.
*G01N 3/24* (2006.01)
(52) U.S. Cl. ............................................. 73/843
(58) Field of Classification Search ............ 73/841–843
See application file for complete search history.

(56) References Cited

U.S. PATENT DOCUMENTS 4,356,732 A * 11/1982 Hachtel et al. ......... 73/862.331
4,768,374 A * 9/1988 Fouchey ................. 73/115.07
6,347,554 B1 * 2/2002 Klingler ................. 73/862.08
6,581,697 B1 * 6/2003 Giardino ........................ 173/1

* cited by examiner

Primary Examiner—Max Noori
(74) Attorney, Agent, or Firm—Ming Chow; Sinorica, LLC (57) ABSTRACT

A torsion detecting mechanism for a pneumatic tool is a torque detecting mechanism which comprises a rack, a driving device, a buffer device, a sensing member and a pressure relieving device. The rack is provided for mounting the driving device, the buffer device, the sensing member, and the pressure relieving device. A pneumatic tool drives the driving device to rotate, such that the buffer device is pressed against the sensing member to obtain the test data, such as the torque of the pneumatic tool. After the test is finished, the pressure relieving device will relieve the oil pressure of the buffer device, enabling the driving device to be immediately returned to the state of waiting for the next test. Thereby, such arrangements not only provide a stable test, an accurate test data, and a high test safety, but also can wide the industrial application.

7 Claims, 7 Drawing Sheets

TORSION DETECTING MECHANISM FOR A PNEUMATIC TOOL

BACKGROUND OF THE INVENTION

1. Field of the Invention

The present invention relates to a torsion detecting mechanism for a pneumatic tool, and more particularly to a torque detecting mechanism which not only provides a stable test, an accurate test data, and a high test safety, but also can wide the industrial application by utilizing the pneumatic tool to drive a sensing member to sense the test data, such as the torque value or life, and a pressure relieving device to return to the state of waiting for the next test.

2. Description of the Prior Art

A conventional torque tester for a pneumatic wrench is disclosed in TW Pat. serial number 094219772 and comprises a pressure device, a connecting device, a measuring device, a sensing device and a processor. The pressure device includes a drive shaft for turning a pneumatic tool. The connecting device is connected to one side of the pressure device and is in communication with the pressure device. The measuring device is disposed at one end of the connecting device and is provided for showing the pressure applied to the pressure device. The sensing device is disposed at the other end of the connecting device opposite to the measuring device for sensing the pressure and converting it into electronic signal to show the torque value, and then the processor receives the torque value from the sensing device to perform statistical processing.

However, the above-mentioned conventional structure still has the following disadvantages:

Firstly, since the pressure device includes a drive shaft for turning a pneumatic tool, the connecting device is connected to one side of the pressure device and is in communication with the pressure device, the measuring device is disposed at one end of the connecting device, and the sensing device is disposed at the other end of the connecting device opposite to the measuring device, such a structure is complex.

Secondly, the measuring device and the sensing device are protruded out of the pressure device, such that the measuring device and the sensing device are likely to be damaged during the test, so the conventional torque tester for a pneumatic wrench is insecure.

Thirdly, since the measuring device cooperates with the sensing device to show the test data, during the test, the torque will be dispersed towards the measuring device and the sensing device. As a result, the test data, such as the torque, is inaccurate, so the conventional torque tester for a pneumatic wrench is imprecise.

Fourthly, the measuring device cooperates with the sensing device to show the test data, during the test, the torque will be dispersed towards the measuring device and the sensing device, so the conventional torque tester for a pneumatic wrench is instable.

Fifthly, the pressure device includes a drive shaft for turning the pneumatic tool, the connecting device is connected to one side of the pressure device and is in communication with the pressure device, and the pressure device is disposed with a medium that can be gas or liquid. And the bigger pressure cylinder of the pressure device needs a large amount of medium, so the test system is instable during the test.

The present invention has arisen to mitigate and/or obviate the afore-described disadvantages.

SUMMARY OF THE INVENTION

The primary objective of the present invention is to provide a torsion detecting mechanism for a pneumatic tool which not only provides a stable test, an accurate test data, and a high test safety, but also can wide the industrial application.

A pneumatic tool directly drives a drive member of a driving device to rotate. The drive member cooperates with a driven member to change the driving direction, such that the driven member linearly pushes a buffer device to transmit the pressure to a sensing member for sensing, so as to change the mode of pressure sensing, thus showing the test result of the pneumatic tool. Thereby, such arrangements not only provide a stable test and an accurate test data, but also can wide the industrial application.

The second objective of the present invention is to provide a torsion detecting mechanism for a pneumatic tool, which is a torque detecting mechanism. A pneumatic tool drives a driving device to rotate, and then the driving device rotates a buffer device, such that the buffer device is pressed against a sensing member to obtain the test data, such as the torque or durable degree of the pneumatic tool. After the test is finished, the pneumatic tool will relieve the gas, and the pressure relieving device will relieve the oil pressure of the buffer device, enabling the driving device to be returned to the state of waiting for the next test. Thereby, such arrangements not only provide a stable test, an accurate test data, and a high test safety, but also can wide the industrial application.

The present invention will become more obvious from the following description when taken in connection with the accompanying drawings, which show, for purpose of illustrations only, the preferred embodiments in accordance with the present invention.

DETAILED DESCRIPTION OF THE PREFERRED EMBODIMENTS

Figure 1:
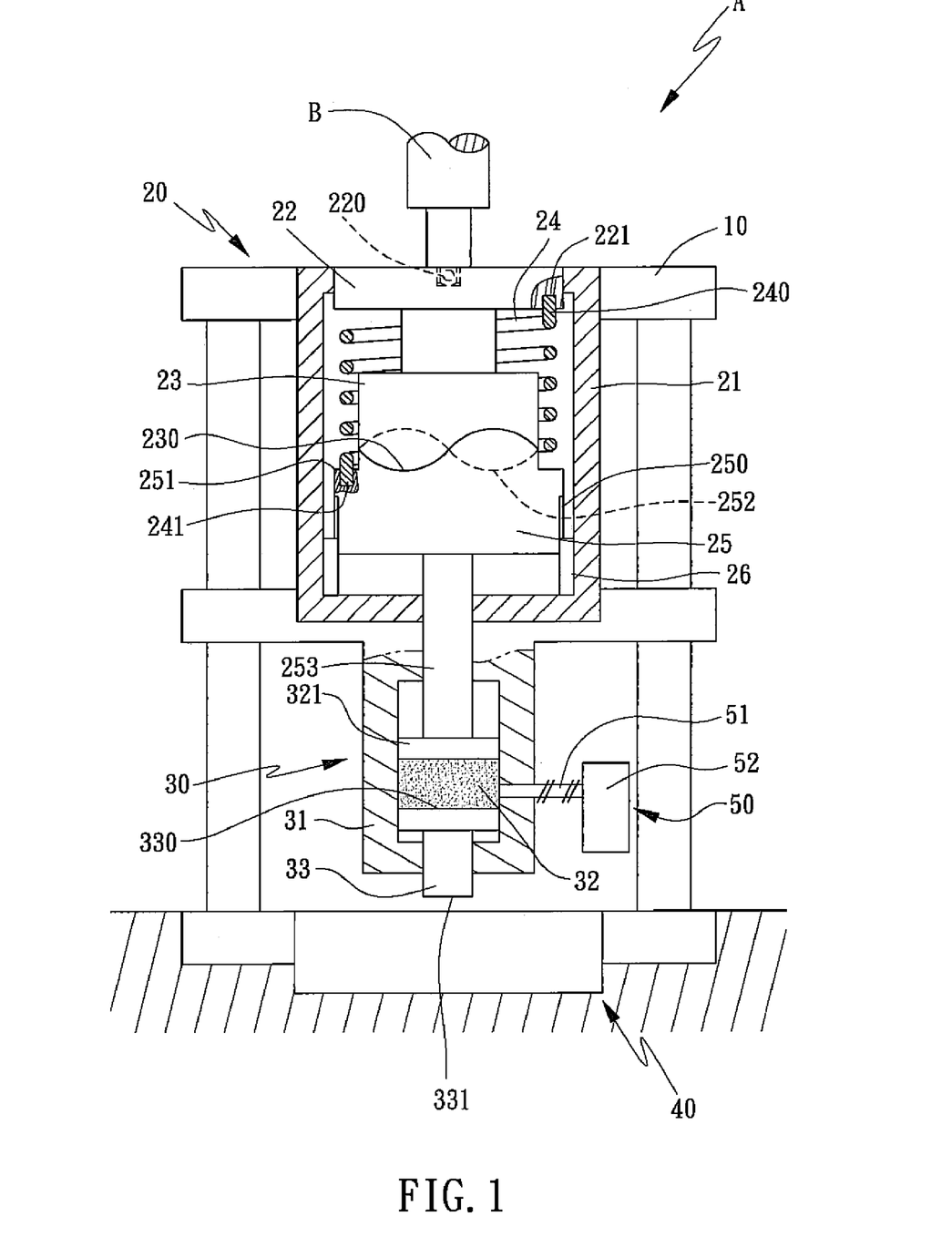
FIG. 1 is a plan view of a torsion detecting mechanism for a pneumatic tool in accordance with a first embodiment of the present invention.
Figure 2:
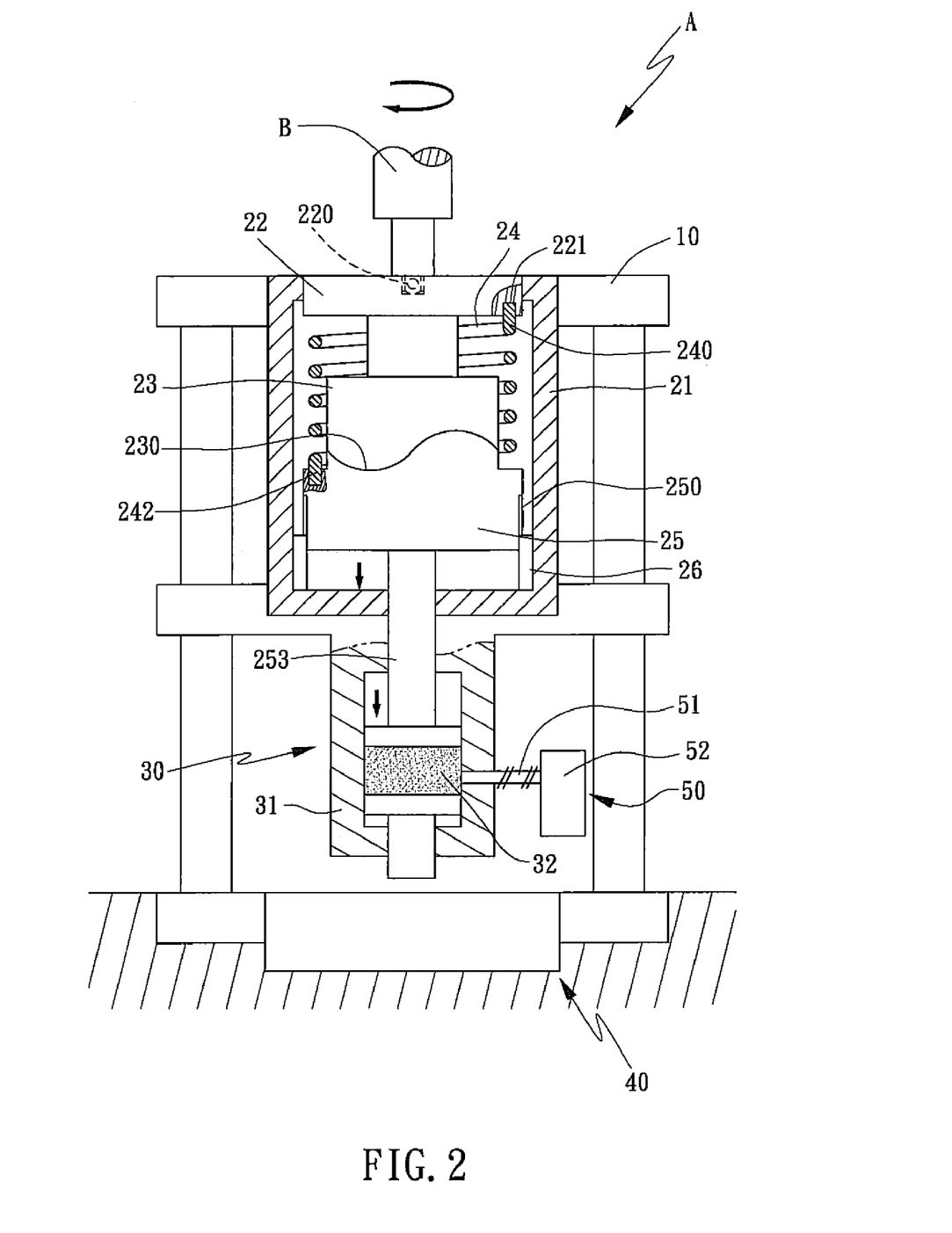
FIG. 2 is an illustrative view showing the torsion detecting mechanism for a pneumatic tool in accordance with the first embodiment of the present invention.

Referring to FIGS. 1 and 2, a torsion detecting mechanism for a pneumatic tool in accordance with a first embodiment of the present invention is a torque detecting mechanism A which comprises a rack 10, a driving device 20, a buffer device 30, a sensing member 40 and a pressure relieving device 50. The rack 10 is provided for mounting the driving device 20, the buffer device 30, and the sensing member 40. The driving device 20 is disposed above the buffer device 30, and the sensing member 40 is disposed at one end of the buffer device 30. A pneumatic tool B drives the driving device 20 to rotate, and then the driving device 20 rotates the buffer device 30, such that the buffer device 30 is pressed against the sensing member 40 to obtain the test data, such as the torque or durable degree of the pneumatic tool B. After the test is finished, the pneumatic tool B will relieve the gas, and the pressure relieving device 50 will relieve the oil pressure of the buffer device 30, enabling the driving device 20 to be returned to the state of waiting for the next test. Thereby, such arrangements not only provide a stable test, an accurate test data, and a high test safety, but also can wide the industrial application.

The rack 10 is a multi-layer structure, a free end of a first layer is provided for fixing the driving device 20, and a mid layer is provided for disposing one end of the buffer device 30. The sensing member 40 is disposed at the other end of the buffer device 30, and the pressure relieving device 50 is disposed at one side of the buffer device 30.

The driving device 20 includes a hollow round containing member 21, a circular-shaped rotating member 22, a reverse T-shaped drive member 23, a wrap type restoration member 24, a reverse T-shaped driven member 25, and a plurality of rectangular-shaped sliding bodies 26. The containing member 21 is defined in the rack 10, and the rotating member 22 is pivotally disposed at a free end of the containing member 21. The rotating member 22 is formed with an inserting portion 220 and a first positioning portion 221. The pneumatic tool B is rotatably inserted in the inserting portion 220, and the first positioning portion 221 is disposed at one end of the rotating member 22 opposite to the inserting portion 220 and is provided for fixing the restoration member 24. One end of the drive member 23 is fixed to the rotating member 22, and the other end of the drive member 23 is formed with a wave-shaped drive portion 230 that abuts against the driven member 25. The restoration member 24 is formed with a first jointing portion 240 and a second jointing portion 241. The first jointing portion 240 is fixed to the first positioning portion 221 of the rotating member 22, and the second jointing portion 241 is fixed to the driven member 25. The driven member 25 is formed with a plurality of groove-shaped sliding portions 250, a second positioning portion 251, a wave-shaped driven portion 252 and a reverse T-shaped pushing portion 253. The sliding portions 250 are slidably disposed in the sliding bodies 26, respectively. The second positioning portion 251 is provided for fixing the second jointing portion 241 of the restoration member 24, and the driven portion 252 abuts against the drive portion 230 of the drive member 23. The sliding bodies 26 are disposed in the inner periphery of the containing member 21 close to the sliding portion 250 of the driven member 25. The pushing portion 253 is disposed at one end of the driven portion 252 and is received in the buffer device 30.

The buffer device 30 includes a rectangular-shaped buffer containing member 31, a fluid medium 32 and a T-shaped abutting member 33. The buffer containing member 31 is disposed at a mid portion of the rack 10, and the pushing portion 253 is received in one end of the buffer containing member 31 close to the driving device 20. The pushing portion 253 of the driven member 25 is used to push the medium 32 of the buffer containing member 31. The medium 32 is disposed between the pushing portion 253 and the abutting member 33 of the buffer containing member 31, and the medium 32 can be gas or liquid. The abutting member 33 is formed with a disk-shaped pushed portion 330 and a column-shaped abutting portion 331. The pushed portion 330 is pushed by the medium 32, and the abutting portion 331 is pressed against the sensing member 40 during the test. And the pressure relieving device 50 is disposed at one side of the buffer containing member 31.

The sensing member 40 serves to convert the test data of the torque and durable degree of the pneumatic tool B into digital value and transmit it to a processor, and then the processor transmits the data to a computer for the user to record.

The pressure relieving device 50 includes a return pipe 51 and a pressure relieving valve body 52 controlled by an electromagnetic valve. One end of the return pipe 51 is connected to the medium 32 of the buffer device 30, and the other end of the return pipe 51 is disposed on the pressure relieving valve body 52.

Figure 3:
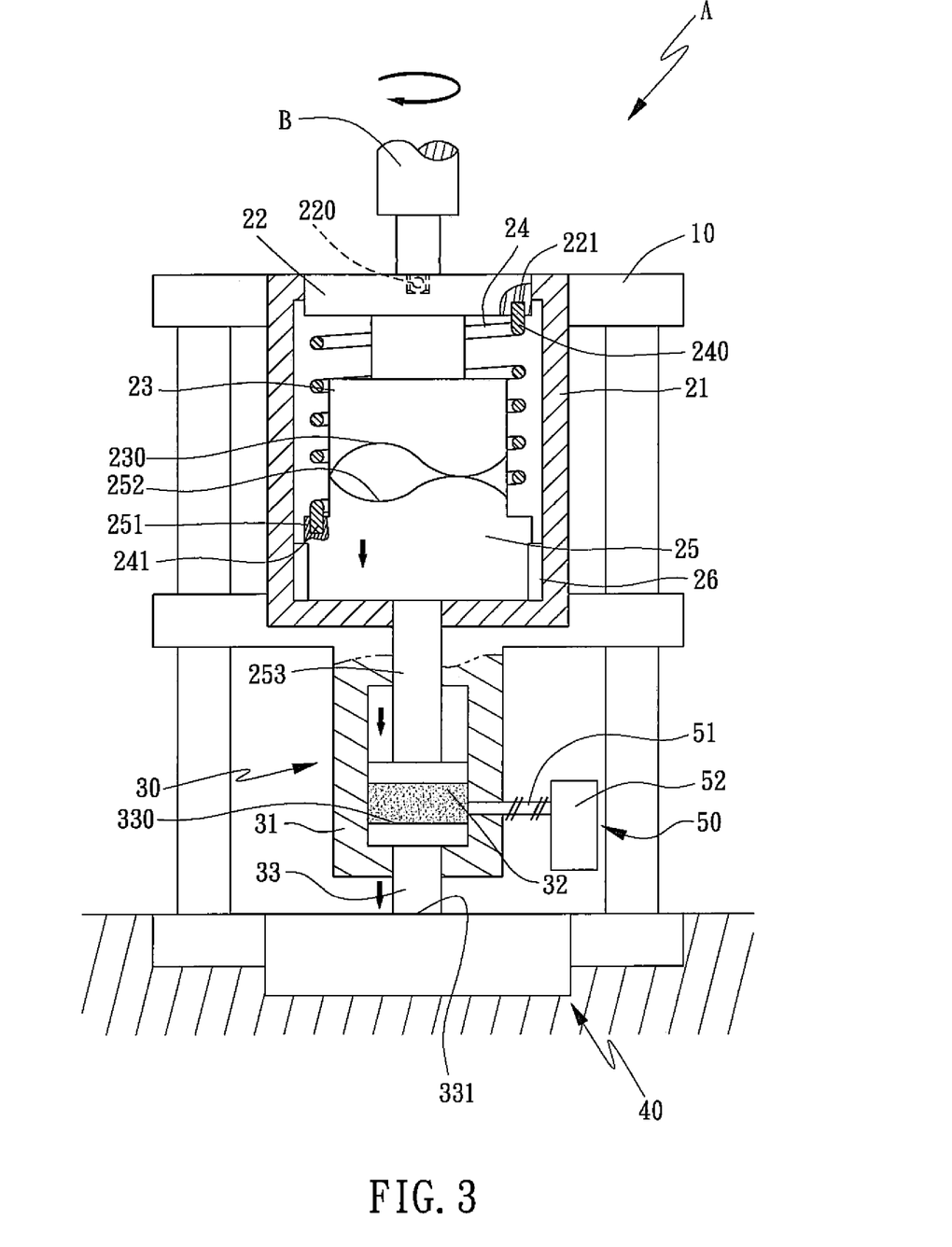
FIG. 3 is an illustrative view showing a first test in accordance with the present invention.
Figure 4:
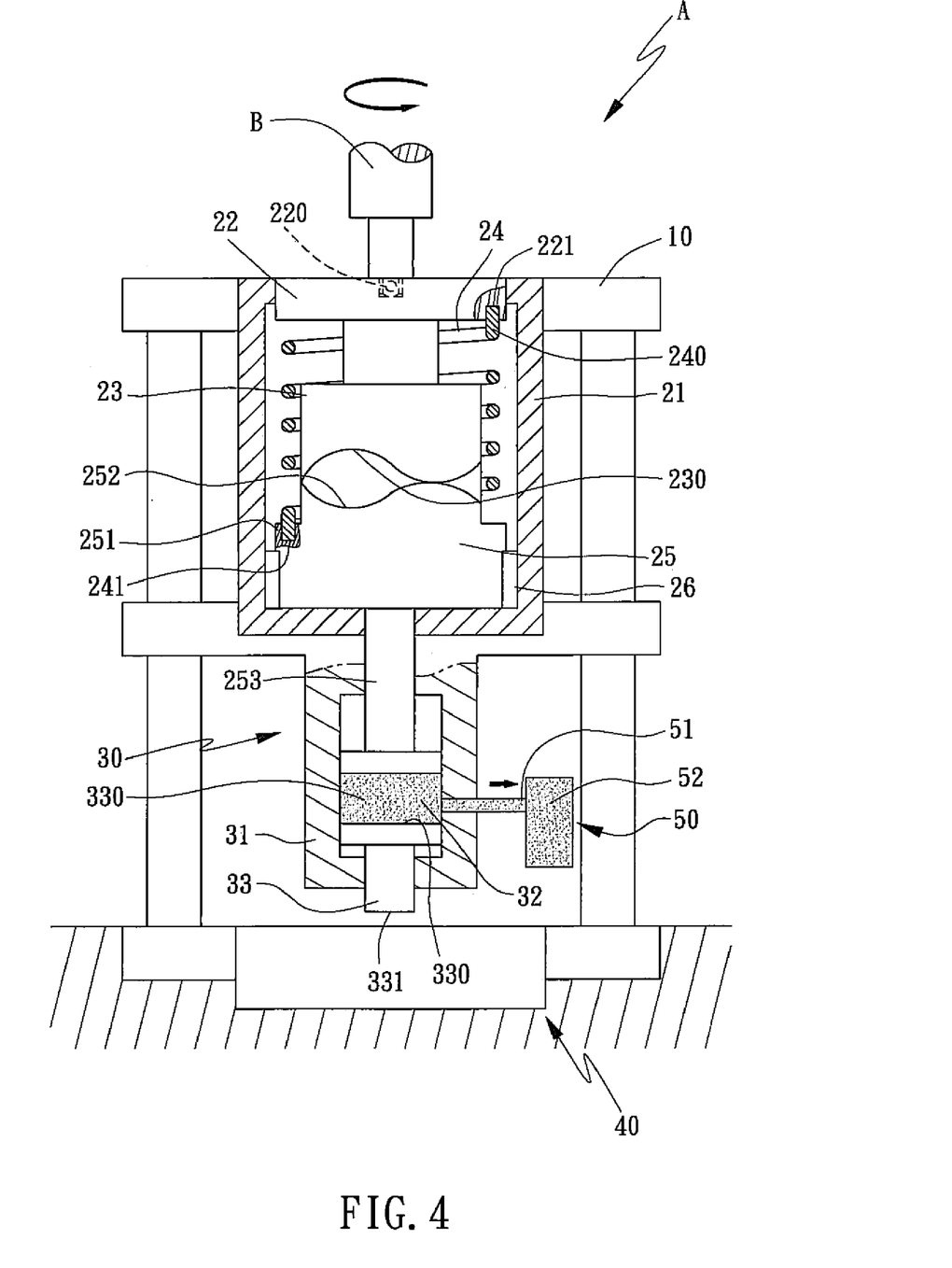
FIG. 4 is an illustrative view showing a second test in accordance with the present invention.
Figure 5:
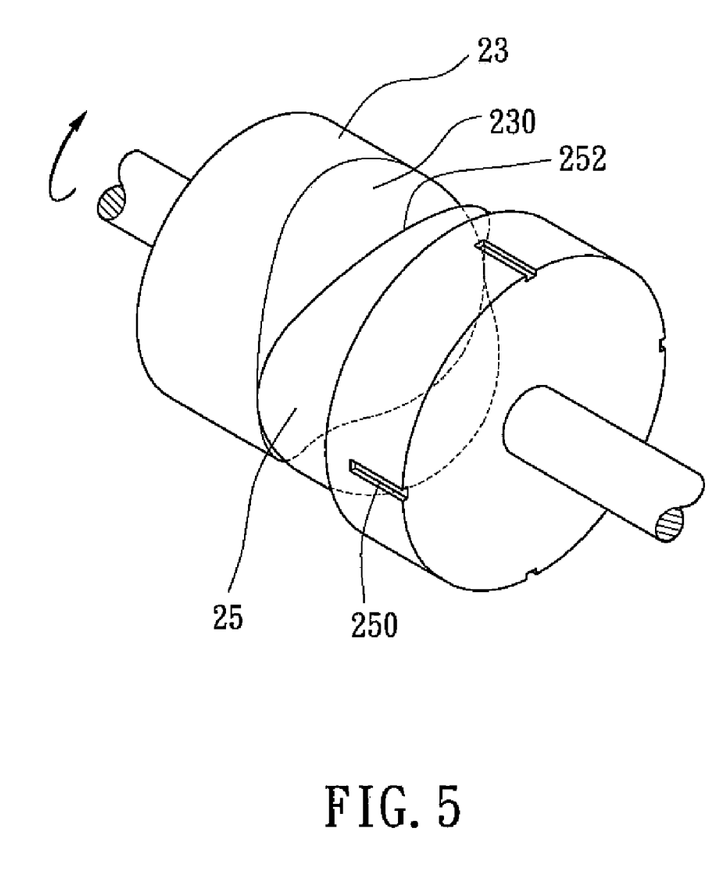
FIG. 5 is an illustrative view showing a driving device in accordance with the present invention.
Figure 6:
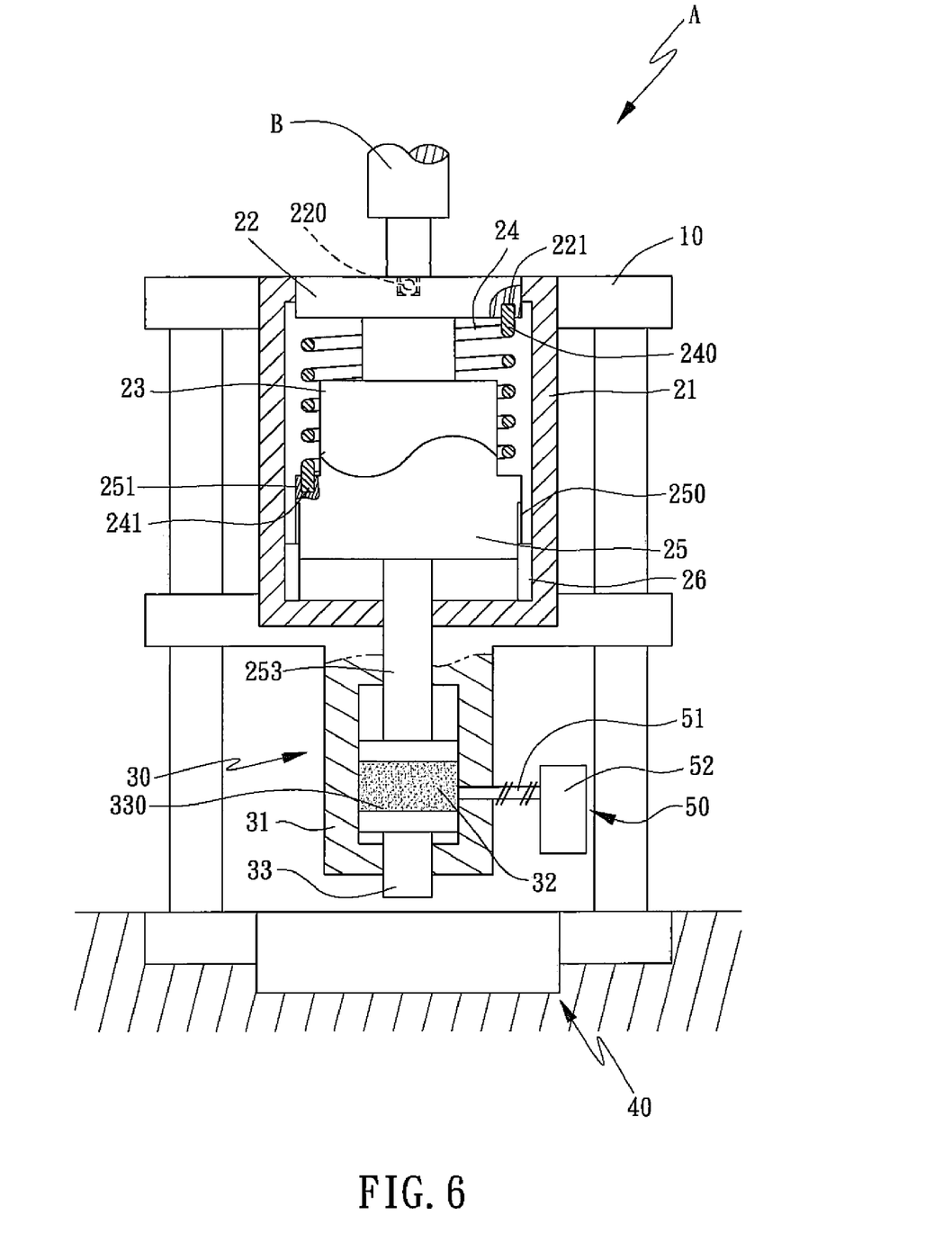
FIG. 6 is an illustrative view showing the torsion detecting mechanism for a pneumatic tool in accordance with the first embodiment of the present invention.

Referring to FIGS. 2-6, the operation of the pneumatic tool B of the present invention is shown. Referring to FIGS. 2 and 3, the pneumatic tool B is rotatably inserted in the inserting portion 220 of the rotating member 20. The pneumatic tool B is rotated by air pressure to drive the rotating member 20 to rotate, and then the rotating member 20 rotates the drive member 23 and the restoration member 24. Referring to FIGS. 3-5, after rotation, the drive portion 230 of the drive member 23 and the driven portion 252 of the driven member 25 are changed from the state of abutting against each other to the state that an arc-shaped height difference is produced therebetween. Further, the sliding portions 250 prevent the driven member 25 from rotating. By such arrangements, the driven member 25 moves downward along the sliding bodies 26. And the pushing portion 253 of the driven member 25 pushes the medium 32 of the buffer device 30, such that the medium 32 will push the pushed portion 330 of the abutting member 33, and then the abutting portion 331 of the abutting member 30 is pressed against the sensing member 40, thus obtaining the test data of torque or durable degree of the pneumatic tool B. Further referring to FIGS. 4 and 6, after the pneumatic tool B is tested, the pressure relieving valve body 52 controlled by the electromagnetic valve is started by the pressure relieving device 50, such that the medium 32 will flow from the return pipe 51 to the pressure relieving valve body 52 of the pressure relieving device 50. And the air pressure of the pneumatic tool B is cut off, so that the drive member 23 and the driven member 25 of the driving device 20 are returned to the state of waiting for the next test by the elasticity of the restoration member 24. In addition, the medium 32 flows between the pushing portion 253 of the driven member 25 of the driving device 20 and the pushed portion 330 of the abutting member 33 from the pressure relieving valve body 52. Thereby, such arrangements not only provide a stable test, an accurate test data, and a high test safety, but also can wide the industrial application.

Figure 7:
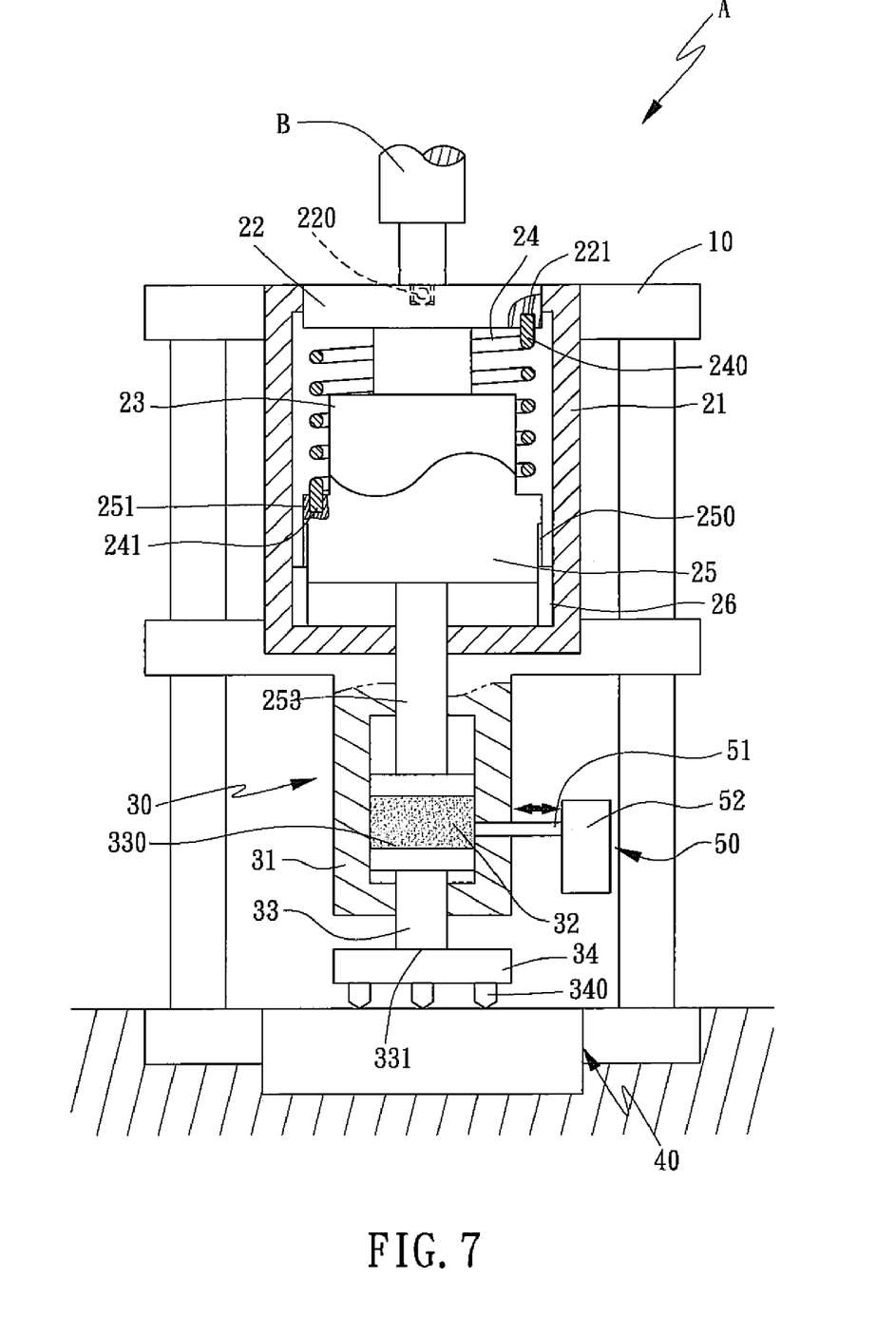
FIG. 7 is an illustrative view showing the torsion detecting mechanism for a pneumatic tool in accordance with a second embodiment of the present invention.

Referring to FIG. 7, a torsion detecting mechanism for a pneumatic tool in accordance with a second embodiment of the present invention is shown. The rack 10 is provided for mounting the driving device 20, the buffer device 30, and the sensing member 40. The driving device 20 is disposed above the buffer device 30, and the sensing member 40 is disposed at one end of the buffer device 30. The abutting member 33 of the buffer device 30 is fixed with a combining body 34, and one end of the combining body 34 is formed with a plurality of cone-shaped abutting members 340. The pneumatic tool B drives the driving device 20 to rotate, and then the driving device 20 rotates the buffer device 30, such that the abutting members 340 of the combining body 34 of the buffer device are pressed against the sensing member 40 to obtain the test data, such as the torque or durable degree of the pneumatic tool B. Thereby, such arrangements not only provide a stable test, an accurate test data, and a high test safety, but also can wide the industrial application.

It is apparent from the above-mentioned descriptions that the present invention has the advantages described as follows:

Firstly, the rack 10 is provided for mounting the driving device 20, the buffer device 30, and the sensing member 40, so the structure of the present invention is simple.

Secondly, since the driving device 20, the buffer device 30, the sensing member 40, and the pressure relieving device 50 are mounted on the same rack 10 without needing to be disposed with an external connected pressure gauge, the present invention has a high test safety.

Thirdly, with the above-mentioned structure, the components of the pneumatic tool B are reduced during the test of the torque detecting mechanism A, so the present invention has a high stability.

Fourthly, the above-mentioned structure enables the components to be reduced, such that the cost of the present invention is reduced.

Fifthly, the pneumatic tool B drives the driving device 20 to rotate, and then the driving device 20 rotates the buffer device 30, such that the abutting portion 331 of the abutting member 33 of the buffer device 30 is pressed against the sensing member 40 to obtain the test data, such as the torque or durable degree of the pneumatic tool B. Moreover, since the pneumatic tool B drives the driving device 20 to rotate, and then the driving device 20 rotates the buffer device 30, the abutting members 340 of the combining body 34 of the buffer device 30 also will be pressed against the sensing member 40 to obtain the test data, such as the torque or durable degree of the pneumatic tool B by the multi-point test. Thereby, the present invention can be tested by multi method.

While we have shown and described various embodiments in accordance with the present invention, it should be clear to those skilled in the art that further embodiments may be made without departing from the scope of the present invention.

What is claimed is:

1. A torsion detecting mechanism for a pneumatic tool, comprising:
   a driving device including a rotating member, the pneumatic tool being rotatably inserted in one end of the rotating member, the other end of the rotating member having a drive portion with an arc-shaped height difference, one end of a driven member being formed with a driven portion opposite to the drive portion, the driven portion having an arc-shaped height difference corresponding to the drive portion, the driven member being moved axially without rotating, the other end of the driven member being formed with a pushing portion, and a restoration member, both ends of the restoration member being fixed to the rotating member and the driven member, respectively;
   a buffer device including a buffer containing member for containing the pushing portion, the pushing portion being used to push a medium disposed between the pushing portion and an abutting member of the buffer containing member, the abutting member being formed with a pushed portion and an abutting portion, the pushed portion being pushed by the medium;
   a sensing member disposed close to the abutting portion of the abutting member of the buffer device;
   a pressure relieving device including a return pipe, one end of the return pipe being connected to the medium of the buffer containing member of the buffer device, and the other end of the return pipe being connected to a pressure relieving valve body.

2. The torsion detecting mechanism for a pneumatic tool as claimed in claim 1, wherein the driving device, the buffer device and the sensing member are disposed on a rack.

3. The torsion detecting mechanism for a pneumatic tool as claimed in claim 1, wherein the medium is a fluid medium including gas or liquid.

4. The torsion detecting mechanism for a pneumatic tool as claimed in claim 1, wherein the driving device includes a containing member, the rotating member is pivotally disposed at one end of the containing member, an inserting portion is defined in one end of the rotating member and is protruded out of the containing member, the other end of the rotating member is formed with a first positioning portion, the pneumatic tool is rotatably inserted in the inserting portion, on end of the restoration member is fixed to the first positioning portion, one end of a drive member is fixed to the rotating member, the other end of the drive member is formed with the wave-shaped drive portion with the arc-shaped height difference, a shape of the driven portion of the driven member is corresponding to that of the drive portion, the driven member is formed with a second positioning portion, a first jointing portion of the restoration member is fixed to the first positioning portion of the rotating member, and a second jointing portion is fixed to the second positioning portion of the driven member.

5. The torsion detecting mechanism for a pneumatic tool as claimed in claim 1, wherein the driving device includes the driven member that is formed with a plurality of sliding portions, a second positioning portion, and the wave-shaped driven portion with the arc-shaped height difference, the sliding portions are formed with a plurality of sliding bodies, the second positioning portion is fixed with a second jointing portion of the restoration member, the driven portion abuts against the drive portion of a drive member, and the sliding bodies are disposed in an inner periphery of a containing member.

6. The torsion detecting mechanism for a pneumatic tool as claimed in claim 2, wherein the driving device includes the driven member that is formed with a plurality of sliding portions, a second positioning portion, and the wave-shaped driven portion with the arc-shaped height difference, the sliding portions are formed with a plurality of sliding bodies, the second positioning portion is fixed with a second jointing portion of the restoration member, the driven portion abuts against the drive portion of a drive member, and the sliding bodies are disposed in an inner periphery of a containing member.

7. The torsion detecting mechanism for a pneumatic tool as claimed in claim 1, wherein the abutting member of the buffer device is fixed with a combining body, the combining body is formed with a plurality of abutting members for pressing against the sensing member during a test.

* * * * *